(12) United States Patent
Lundkvist et al.

(10) Patent No.: US 8,597,344 B2
(45) Date of Patent: *Dec. 3, 2013

(54) RADIOPAQUE SUPER-ELASTIC INTRAVASCULAR STENT

(75) Inventors: Andre S. Lundkvist, Hayward, CA (US); David A. Watson, San Jose, CA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/709,734

(22) Filed: Feb. 22, 2010

(65) Prior Publication Data

US 2010/0152837 A1    Jun. 17, 2010

Related U.S. Application Data

(62) Division of application No. 11/970,338, filed on Jan. 7, 2008.

(51) Int. Cl.
*A61F 2/06* (2013.01)

(52) U.S. Cl.
USPC ....... 623/1.22; 623/1.15; 623/1.31; 623/1.34; 623/1.44; 623/1.46

(58) Field of Classification Search
USPC ............. 623/1.22, 1.35, 1.15, 1.18, 1.2, 1.33, 623/1.42, 1.44, 1.46
See application file for complete search history.

(56) References Cited

U.S. PATENT DOCUMENTS

| | | | |
|---|---|---|---|
| 2,841,546 A | 7/1958 | Robinson | |
| 3,306,088 A | 2/1967 | Adler et al. | |
| 3,465,429 A | 9/1969 | Barber et al. | |
| 3,509,617 A | 5/1970 | Winter | |
| 3,742,588 A | 7/1973 | George | |
| 3,841,127 A | 10/1974 | Pashak | |
| 3,874,066 A | 4/1975 | Lanner | |

(Continued)

FOREIGN PATENT DOCUMENTS

| | | |
|---|---|---|
| JP | 10066730 | 3/1998 |
| JP | 2006515779 T | 6/2006 |
| WO | 2006124541 | 11/2006 |

OTHER PUBLICATIONS

"Carotid Artery Balloon Angioplasty and Stenting (CABAS): A Neuroradiologic Perspective", AJNR, Sep. 1998, vol. 19, pp. 1535-1539.

(Continued)

*Primary Examiner* — David Isabella
*Assistant Examiner* — Yashita Sharma
(74) *Attorney, Agent, or Firm* — Fulwider Patton LLP

(57) ABSTRACT

The intravascular stent is formed from a composite wire includes an inner core of radiopaque metal, a polymer layer coaxially disposed about the inner core, and an outer metal layer coaxially disposed about the polymer layer. The intermediary polymer layer acts as a barrier material between the inner core and the outer sheath, so that the inner core and outer sheath may be made of dissimilar metallic layers, and the intermediary polymer layer will prevent a galvanic reaction between the inner core and the peripheral metal layer. The intravascular stent has ends flared radially outwardly to prevent radially and longitudinally inward deformation of the ends of the stent when the stent is disposed in a desired location in a patient's vasculature.

17 Claims, 3 Drawing Sheets

(56) References Cited

U.S. PATENT DOCUMENTS

| | | | |
|---|---|---|---|
| 3,890,701 A | 6/1975 | Diepers | |
| 4,224,085 A | 9/1980 | Brendel et al. | |
| 4,270,373 A | 6/1981 | Hirato et al. | |
| 4,438,155 A | 3/1984 | Kawai et al. | |
| RE32,399 E | 4/1987 | Nagai et al. | |
| 4,659,310 A | 4/1987 | Kottemann | |
| 4,686,153 A | 8/1987 | Tominaga et al. | |
| 4,734,300 A | 3/1988 | Simanyi et al. | |
| 4,819,618 A | 4/1989 | Liprie | |
| 4,837,416 A | 6/1989 | Yamamoto et al. | |
| 4,865,933 A | 9/1989 | Blanyer et al. | |
| 4,889,107 A | 12/1989 | Kaufman | |
| 4,917,965 A | 4/1990 | Inoue et al. | |
| 5,041,041 A | 8/1991 | Passmore et al. | |
| 5,045,527 A | 9/1991 | Ikeno et al. | |
| 5,360,440 A * | 11/1994 | Andersen | 607/115 |
| 5,441,516 A | 8/1995 | Wang et al. | |
| 5,554,181 A | 9/1996 | Das | |
| 5,628,787 A | 5/1997 | Mayer | |
| 5,630,840 A | 5/1997 | Mayer | |
| 5,674,276 A | 10/1997 | Andersen | |
| 5,679,470 A | 10/1997 | Mayer | |
| 5,725,570 A | 3/1998 | Heath | |
| 5,800,511 A | 9/1998 | Mayer | |
| 5,824,077 A | 10/1998 | Mayer | |
| 6,027,528 A | 2/2000 | Tomonto et al. | |
| 6,086,611 A * | 7/2000 | Duffy et al. | 623/1.35 |
| 6,165,194 A | 12/2000 | Denardo | |
| 6,241,691 B1 | 6/2001 | Ferrera et al. | |
| 6,287,331 B1 | 9/2001 | Heath | |
| 6,287,333 B1 | 9/2001 | Appling et al. | |
| 6,290,721 B1 | 9/2001 | Heath | |
| 6,475,235 B1 | 11/2002 | Jayaraman | |
| 6,485,524 B2 | 11/2002 | Strecker | |
| 6,497,671 B2 | 12/2002 | Ferrera et al. | |
| 6,527,802 B1 | 3/2003 | Mayer | |
| 6,530,949 B2 | 3/2003 | Konya et al. | |
| 6,652,574 B1 | 11/2003 | Jayaraman | |
| 6,746,478 B2 | 6/2004 | Jayaraman | |
| 6,926,733 B2 | 8/2005 | Stinson | |
| 7,000,305 B2 | 2/2006 | Jayaraman | |
| 7,102,143 B2 | 9/2006 | Leblans et al. | |
| 2001/0039446 A1 * | 11/2001 | Edwin et al. | 623/1.13 |
| 2002/0035396 A1 | 3/2002 | Heath | |
| 2003/0093141 A1 * | 5/2003 | Dimatteo et al. | 623/1.13 |
| 2005/0067584 A1 | 3/2005 | Bergh et al. | |
| 2005/0096733 A1 * | 5/2005 | Kovneristy et al. | 623/1.22 |
| 2005/0137693 A1 | 6/2005 | Haug et al. | |
| 2005/0209680 A1 | 9/2005 | Gale et al. | |
| 2006/0224142 A1 | 10/2006 | Wilson et al. | |
| 2006/0276887 A1 | 12/2006 | Brady et al. | |
| 2007/0021685 A1 | 1/2007 | Oepen et al. | |
| 2007/0179592 A1 | 8/2007 | Schaeffer | |
| 2008/0147111 A1 * | 6/2008 | Johnson et al. | 606/200 |
| 2009/0216307 A1 | 8/2009 | Kaufmann et al. | |

OTHER PUBLICATIONS

"Conformexx—Innovation Taking Shape", http://www.bardpv.com/_united/product.php?p=74, C. R. Bard, Inc., last accessed Feb. 13, 2007.

"Mems & Moems Packaging Challenges", by Dr. Ken Gilleo, Cookson Electronics, ET-Trends, Jan. 11, 2001.

Notification of Reasons for Refusal, Jan. 29, 2013, 3 pages.

* cited by examiner

RADIOPAQUE SUPER-ELASTIC INTRAVASCULAR STENT

CROSS-REFERENCES TO RELATED APPLICATIONS INVENTION

This application is a divisional of co-pending application Ser. No. 11/970,338 filed on Jan. 7, 2008.

BACKGROUND OF THE INVENTION

This invention relates generally to implantable vasoocclusive devices for interventional therapeutic treatment or vascular surgery, and more particularly concerns a radiopaque super-elastic intravascular stent formed from a composite wire with enhanced radiopacity and increased corrosion resistance. The intravascular stent has superelastic or shape memory properties and improved radiopaque properties for visible detection under fluoroscopy, and the ends of the stent are flared radially outwardly to prevent radially and longitudinally inward deformation of the ends of the stent when the stent is stretched or disposed in a desired location in a patient's vasculature.

Vasoocclusive devices are therapeutic devices that are placed within the vasculature of the human body, typically via a catheter, either to block the flow of blood through a vessel making up that portion of the vasculature through the formation of an embolus or to form such an embolus within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration that may be dimensioned to engage the walls of the vessels.

The vasoocclusive devices, which can have a primary shape of a coil of wire that is then formed into a more complex secondary shape, can be produced in such a way that they will pass through the lumen of a catheter in a linear shape and take on a complex shape as originally formed after being deployed into the area of interest, such as an aneurysm. A variety of detachment mechanisms to release the device from a pusher have been developed and are known in the art.

For treatment of areas of the small diameter vasculature such as a small artery or vein in the brain, for example, and for treatment of aneurysms and the like, microcoils formed of very small diameter wire are used in order to restrict, reinforce, or to occlude such small diameter areas of the vasculature. A variety of materials have been suggested for use in such microcoils, including nickel-titanium alloys, copper, stainless steel, platinum, tungsten, various plastics or the like, each of which offers certain benefits in various applications. Nickel-titanium alloys are particularly advantageous for the fabrication of such microcoils, in that they can have super-elastic or shape memory properties, and thus can be manufactured to easily fit into a linear portion of a catheter, but attain their originally formed, more complex shape when deployed. However, nickel-titanium alloy wires are also not radiopaque in small diameters, and a single nickel-titanium wire would need to be approximately 0.012 inches in diameter to be even slightly radiopaque. However, such a thickness of a single nickel-titanium wire would unfortunately also be relatively stiff and possibly traumatic to the placement site, particularly if used for treatment of delicate and already damaged areas of the small diameter vasculature such as an aneurysm in an artery or vein in the brain, for example.

One known type of stent includes a metal filament material formed of a metal outer member and an inner core formed of a different metal than the outer member. Another type of stent is formed of multiple filaments, each of which is a composite including a central core formed of a radiopaque and relatively ductile material such as tantalum or platinum allowing in vivo imaging of the stent, and an outer case formed of a relatively resilient material, such as a cobalt/chromium based alloy. An intermediate barrier layer of tantalum, niobium or platinum may be placed between the case and core, when the core and case materials would be incompatible if contiguous, due to a tendency to form intermetallics. A radiopaque case may surround the core, or to improve compatibility, a biocompatible cover layer, such as one or more of tantalum, platinum, iridium, stainless steel, niobium and titanium can surround the case.

Another type of endoprosthesis in the form of an elongated wire member is known that includes a central cylindrical or tubular core and an outer tubular sheath. An intermediate tubular layer may be disposed between the inner tubular layer and the outer tubular layer. The tube may include outer and inner layers formed of one material such as cobalt, carbon, manganese, silicon, phosphorus, sulfur, chromium, nickel, molybdenum, titanium, iron, alloys thereof and combination thereof, and an intermediate layer between the outer and inner layers formed of another material, such as gold, platinum, tantalum, iridium, tungsten, and alloys thereof and combination thereof.

Another type of stent preform includes an elongated metal core of a shape-memory alloy with a solid cross section, and a hollow outer sheath made of a biocompatible polymer such as a heat-shrinkable polymer material or polymer tape to prevent the core from directly contacting the body lumen. In another type of stent perform, an intermediate sleeve of a lubricious lining is disposed between the core and outer sheath.

Another type of stent is known that is made from multiple knitted or braided wire strands made of materials such as stainless steel, tungsten, titanium, nickel titanium alloy, gold or silver, coated on the outside with a biocompatible fluoropolymer.

While nickel-titanium wire such as nitinol wire has important shape memory and superelastic properties that are useful in vasoocclusive devices and stents, this material is not very radiopaque, so that it would be desirable to utilize a more radiopaque material that can be visualized under fluoroscopy. More radiopaque materials typically do not have shape memory and superelastic properties suitable for forming in vasoocclusive devices and stents, and combining such radiopaque materials with nickel-titanium wire such as nitinol wire are typically prone to galvanic corrosion, resulting in failure or compromise of the larger wire or the larger assembled system. It has also been found that when an intravascular stent is stretched longitudinally, the stent will naturally shrink in diameter, but will not shrink uniformly, in that the ends of the stent will commonly shrink in diameter to a greater extent than the diameter of a central body portion of the stent shrinks, resulting in a condition referred to as "fishmouthing" of the stent.

It would thus be desirable to provide an intravascular stent formed from a structural element that offers the advantages of a shape memory alloy such as a nickel-titanium alloy, and that incorporates radiopaque material, so that the intravascular stent can be visualized under fluoroscopy, and that is not subject to galvanic corrosion during use of the device. It would also be desirable to provide an intravascular stent that will resist radially and longitudinally inward deformation of the ends of the stent when the stent is stretched or disposed in a desired location in a patient's vasculature. The present invention meets these and other needs.

SUMMARY OF THE INVENTION

Briefly, and in general terms, the present invention provides for a generally tubular intravascular stent with a plurality of end loop portions at opposing first and second ends of the stent, and an intermediate tubular body portion formed of a plurality of intermediate circumferential loops between the plurality of end loop portions. The intermediate tubular body portion has a first diameter, an enlarged first end and an enlarged opposing second end, and the enlarged first and second ends have a second diameter greater than the first diameter of the intermediate tubular body portion. In a presently preferred aspect, a plurality of the end loop portions flare radially outward with respect to the intermediate tubular body portion of the stent. In another preferred aspect, the plurality of end loop portions and the plurality of intermediate circumferential loops of the intermediate tubular body portion are formed from a single spirally wound composite wire. The composite wire has a first free end and a second free end placed in close proximity to each other, and a short segment of heat shrink tubing is used to capture the first and second free ends together to prevent the free ends of the composite wire from extending away from the body of the stent. The intravascular stent takes on a linear shape when stretched, without the ends shrinking to a diameter less than the diameter of the central body of the stent.

In another presently preferred aspect, the composite wire may be formed as a cylindrical wire, and includes an elongated inner core having a selected length and formed from a radiopaque metal, an intermediate polymer layer coaxially disposed immediately adjacent to and surrounding the inner core, and an outer metal layer coaxially disposed immediately adjacent to and surrounding the polymer layer. The radiopaque metal may be selected from the group consisting of platinum, tantalum, gold, and combinations thereof, and the inner core is typically cylindrical, although other shapes may be suitable for forming the inner core. In a preferred aspect, the inner core is disposed centrally along a longitudinal axis of the composite wire.

In another preferred aspect, the polymer layer may be formed from a polymer selected from the group consisting of polytetrafluoroethylene, poly-para-xylylene, a fluorine substituted poly-para-xylylene, and combinations thereof, while the outer metal layer may be formed of a superelastic alloy, such as nitinol, for example. In another aspect, the inner core and outer sheath may be made of dissimilar metals.

In another aspect, the present invention provides for a cylindrical mandrel including a cylindrical main body having first and second opposing ends and a longitudinal axis, a first set of four orthogonally arranged pegs extending from the cylindrical main body at the first end of the cylindrical main body, and a second set of four orthogonally arranged pegs extending from the cylindrical main body at the second end of the cylindrical main body. A first conical end cap is mounted to the first end of the cylindrical main body, and a second conical end cap mounted to the second end of the cylindrical main body. In a presently preferred aspect, the first and second conical end caps have conically tapered surfaces forming a tapered angle at the first and second ends of the cylindrical main body, and in another aspect the tapered angle is about 30° with respect to the longitudinal axis of the cylindrical main body.

In another presently preferred aspect, the invention provides for a method for forming an intravascular stent, including the steps of winding a single composite wire about a first peg of the first set of pegs of the mandrel at the first end of the mandrel to form a first end loop portion at the first end of the stent, and thereafter transitioning to form an intermediate circumferential loop; winding the composite wire about a first peg of the second set of pegs at the second end of the cylindrical mandrel to form a first end loop portion at the second end of the stent, and thereafter transitioning to form an intermediate circumferential loop; and repeating these steps to continue sequentially to form a plurality of intermediate circumferential loops between a plurality of end loop portions at the opposing first and second ends of the mandrel.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
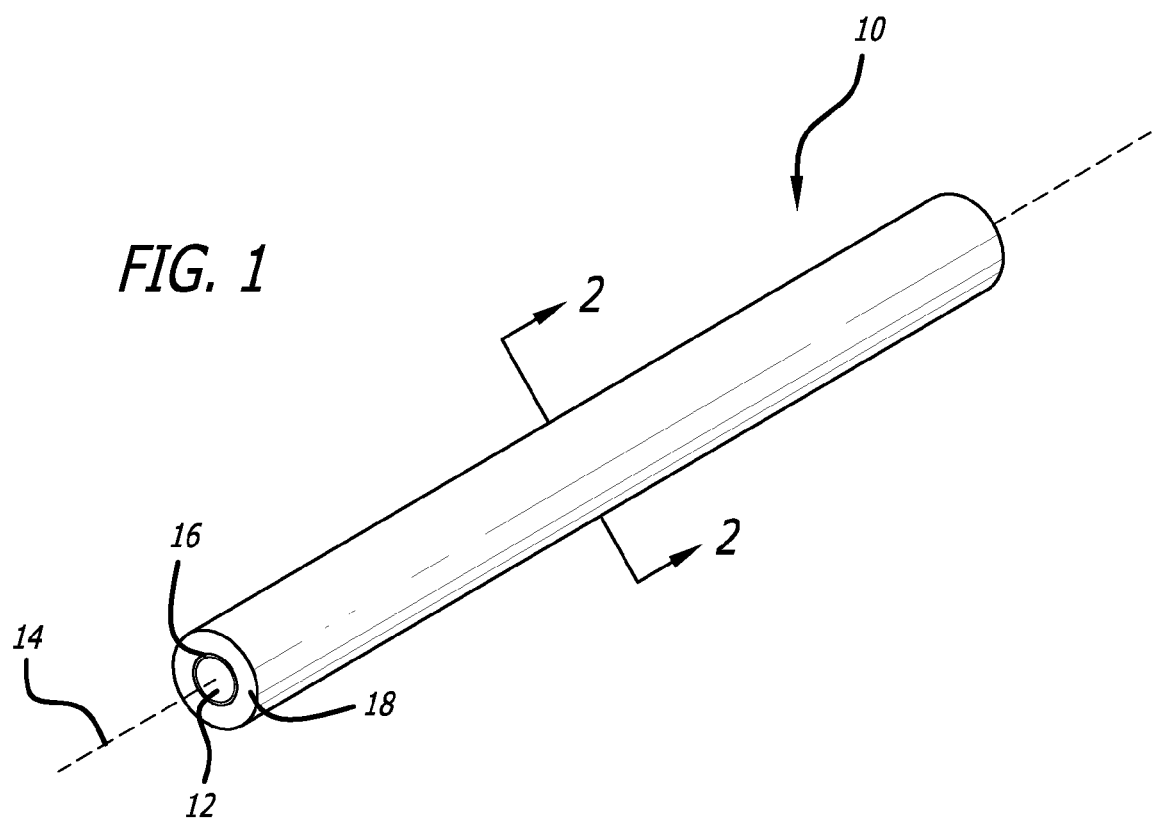
FIG. 1 is a perspective view of a selected length of a composite wire according to the present invention.
Figure 2:
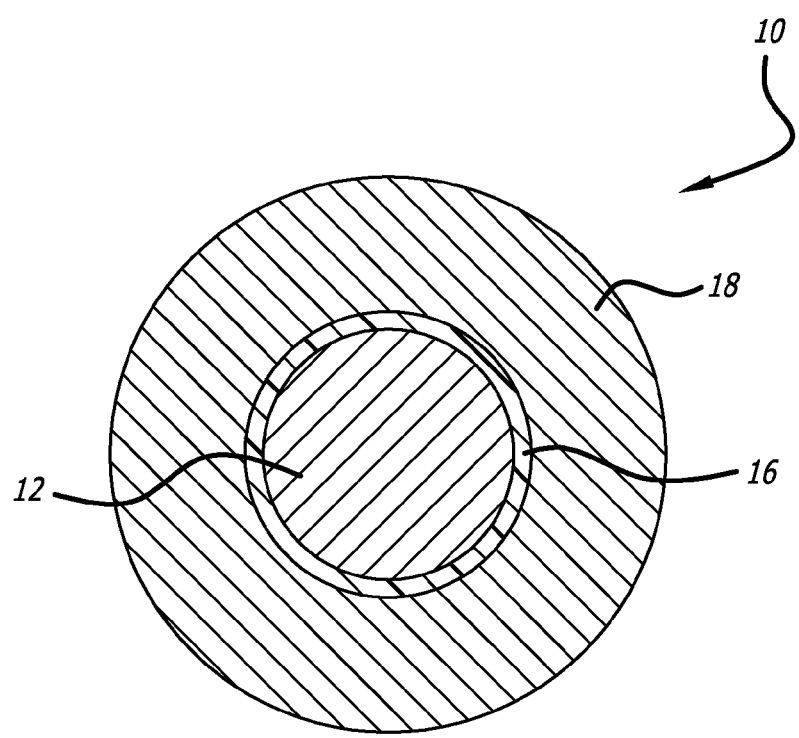
FIG. 2 is a cross sectional view of the composite wire taken along line 2-2 of FIG. 1.

As is illustrated in the drawings, which are provided for the purposes of illustration and not by way of limitation, the invention is embodied in a radiopaque super-elastic intravascular stent 8, illustrated in FIGS. 3-6, formed from a composite wire for forming a vascular interventional device, such as intravascular stents, embolization coils and guidewires, for example. Referring to FIGS. 1 and 2, the composite wire 10 includes an elongated inner core 12 having a selected length and formed from a radiopaque metal, such as, but not limited to, platinum, tantalum, gold, or combinations thereof, for example. The inner core is preferably cylindrical in configuration although other shapes may be used in forming the core, and the inner core is preferably disposed centrally along a longitudinal axis 14 of the composite wire, although alternatively the inner core may be displaced from the central longitudinal axis of the composite wire.

Immediately adjacent to and surrounding the inner core is an intermediate polymer layer 16 that is preferably coaxially disposed about the inner core. The intermediate polymer layer is formed by a thin continuous polymeric layer of material such as, but not limited to, polytetrafluoroethylene (PTFE), poly-para-xylylene (parylene), or its high temperature resistant derivatives, such as a fluorine substituted poly-para-xylylene (parylene HT), for example, or combinations thereof.

Immediately adjacent to and surrounding the intermediate polymer layer is an outer metal layer 18 that is preferably coaxially disposed about the intermediate polymer layer. In a presently preferred aspect, the inner core and the outer metal layer are made of dissimilar metals, and the outer metal layer is formed of a superelastic alloy, such as nitinol, for example, although other metallic materials may be used for forming the outer metal layer. The intermediate polymer layer advantageously insulates the metallic core and outer metal layer from galvanic corrosion.

Figure 3:
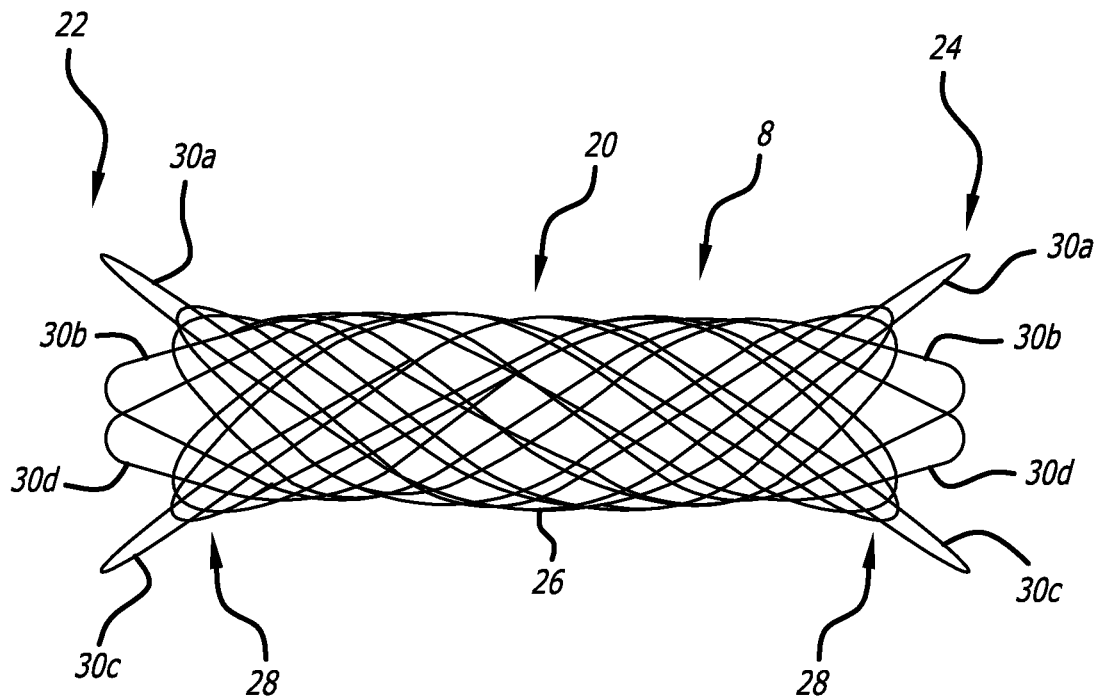
FIG. 3 is a top plan view of a radiopaque super-elastic intravascular stent formed from a composite wire according to the present invention.
Figure 4:
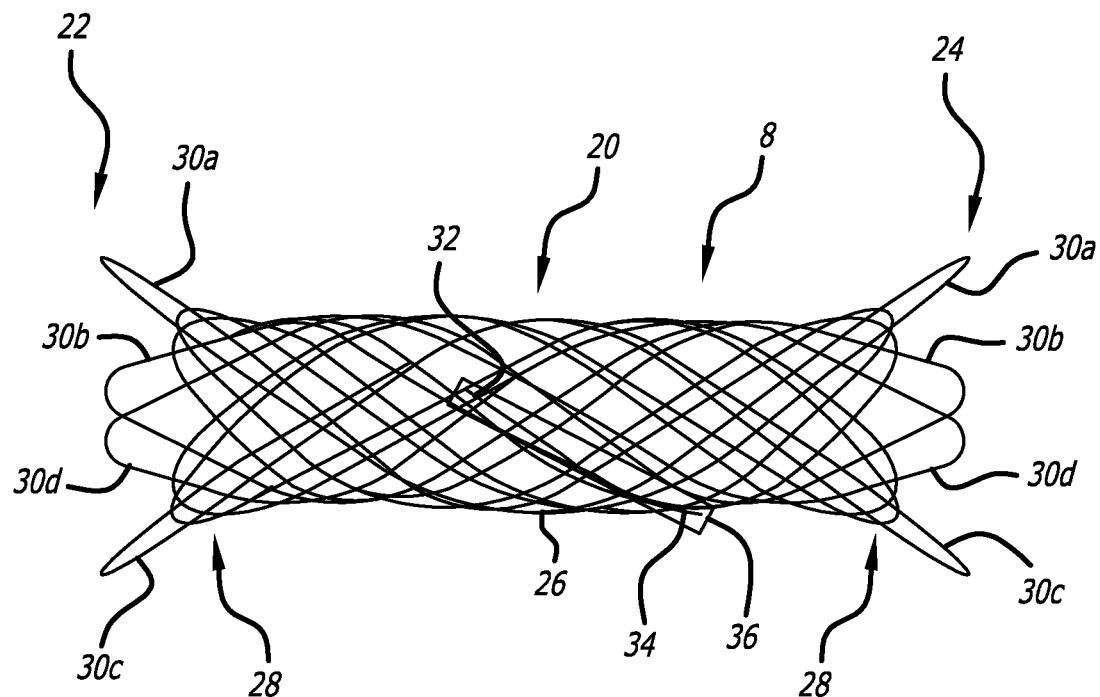
FIG. 4 is a side elevational view of the radiopaque super-elastic intravascular stent of FIG. 3.
Figure 5:
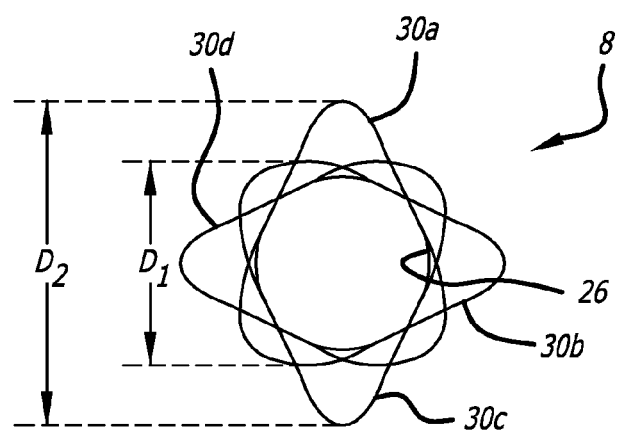
FIG. 5 is an end view of the radiopaque super-elastic intravascular stent of FIG. 3.

Referring to FIGS. 3-5, the intravascular stent is formed in a generally tubular shape having an intermediate tubular body portion 20 having a first diameter $D_1$, an enlarged first end 22 and an enlarged opposing second end 24. The enlarged first and second ends preferably have a second diameter $D_2$ greater than the first diameter of the intermediate tubular body portion. The intravascular stent is currently preferably formed from a single composite wire spirally wound to form a plurality of intermediate circumferential loops 26 between a plurality of end loop portions 28 at the opposing first and second ends of the stent. In another presently preferred aspect, a plurality of the end loop portions 30a, 30b, 30c, 30d flare radially outward with respect to the intermediate tubular body portion of the stent. The flared intravascular stent typically takes on a linear shape when stretched, without the ends shrinking to a diameter less than the diameter of the central body of the stent.

With reference to FIG. 4, the composite wire that forms the intravascular stent has a first free end 32 and a second free end 34 that are placed in close proximity to each other, and are captured together within a short segment of heat shrink tubing 36 to prevent the free ends of the composite wire from extending away from the body of the stent.

Figure 6:
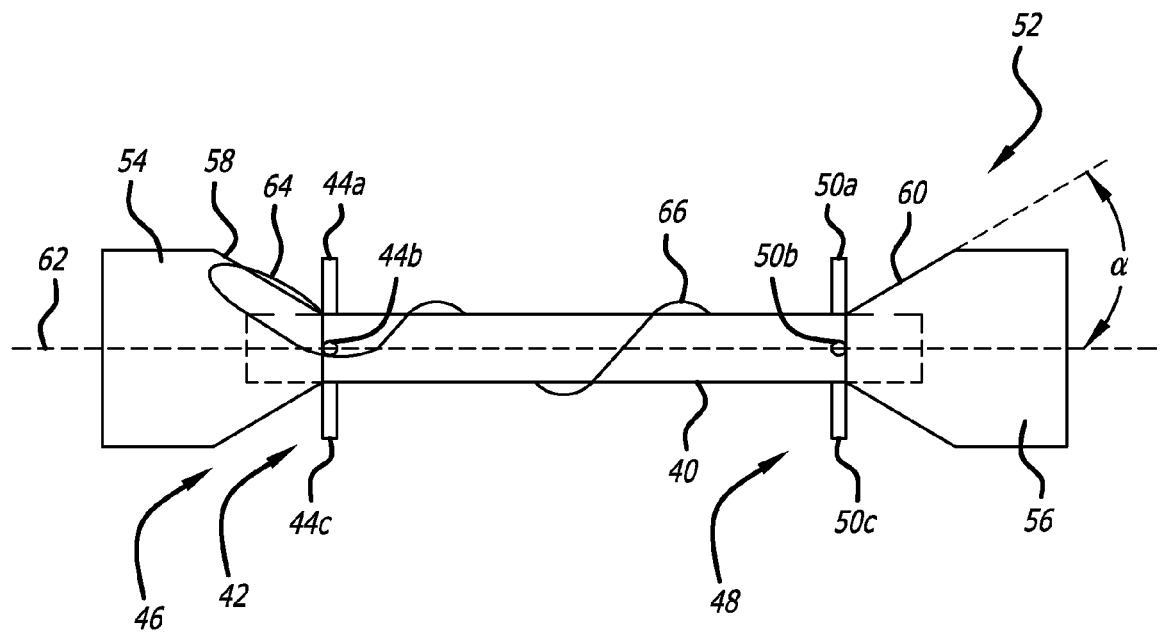
FIG. 6 is a side elevational view of a mandrel for winding the radiopaque super-elastic intravascular stent of FIG. 3.

As is illustrated in FIG. 6, the intravascular stent is formed by winding a length of the single composite wire spirally about a cylindrical mandrel 40 having a first set 42 of four orthogonally arranged pegs 44a, 44b, 44c, 44d (hidden) extending from the mandrel at the first end 46 of the mandrel, and a second set 48 of four orthogonally arranged pegs 50a, 50b, 50c, 50d (hidden) extending from the mandrel at the second end 52 of the mandrel. A first conical end cap 54 and a second conical end cap 56 are mounted to the first and second ends of the mandrel. The first and second conical end caps have conically tapered surfaces 58, 60 forming an angle α typically of about 30° with respect to the longitudinal axis 62 of the mandrel at the first and second ends of the mandrel, to provide radially outwardly flaring surfaces for shaping the outwardly flaring end loops of the intravascular stent.

According to the method of the invention, a single composite wire is wound about a first peg 44b of the first set of pegs at the first end of the mandrel to form a first end loop portion 64 at the first end of the stent, thereafter transitioning to form an intermediate circumferential loop 66. The composite wire is then wound about a first peg 50c of the second set of pegs at the second end of the mandrel to form a first end loop portion (hidden) at the second end of the stent, thereafter transitioning to form another intermediate circumferential loop, and so on, continuing sequentially in this manner thereafter to form the plurality of intermediate circumferential loops between a plurality of end loop portions at the opposing first and second ends of the stent. As will be readily apparent, the winding may begin at any stage, such as by first winding about the cylindrical mandrel to form an intermediate circumferential loop, followed by winding about a peg at an end of the mandrel to form an end loop portion, and so on sequentially in this manner.

The radiopaque super-elastic intravascular stent of the present invention is designed to be deployed intravascularly without the necessity of balloons or other expansive elements, and can be deployed from a guiding catheter directly into the area to be treated. The intravascular device of the present invention is particularly useful for treatment of damaged arteries incorporating aneurysms and the like, particularly those which are treatable by the use of embolic coils or other embolic devices or agents used to occlude the aneurysm. More particularly, the intravascular stent of the invention is particularly well adapted to use with the types of catheters used to place such embolic coils in aneurysms, and the device may be used to reinforce the area in the vicinity of an aneurysm while allowing placement of one or more embolic coils through the gaps in the stent, and while assisting in the retention of the embolic devices within a dome of the aneurysm.

It will be apparent from the foregoing that while particular forms of the invention have been illustrated and described, various modifications can be made without departing from the spirit and scope of the invention. Accordingly, it is not intended that the invention be limited, except as by the appended claims.

The invention claimed is:

1. A composite wire, comprising:
   a single wire having a first free end, a second free end, and a main body length therebetween for forming a vascular interventional device, said single wire including:
      an elongated inner core having a selected length and formed from a radiopaque metal;
      an outer metal layer disposed around said elongated inner core along the length of said elongated inner core, wherein said elongated inner core and said outer metal layer are made of dissimilar metals; and
      a continuous intermediate polymer layer disposed between said outer metal layer and said elongated inner core, said continuous intermediate polymer layer being configured to insulate said elongated inner core and said outer metal layer from galvanic corrosion between said elongated inner core and said outer metal layer, and said continuous intermediate polymer layer being formed from a polymer selected from the group consisting of poly-para-xylylene, a fluorine substituted poly-para-xylylene and combinations thereof; and
   a segment of tubing joining the first free end of said single wire and the second free end of said single wire together, said first and second free ends of said single wire being in close proximity to each other such that said segment of tubing joining the first free end of said single wire and the second free end of said single wire together is configured to prevent said first and second free ends of said single wire from extending away from the main body length of said single wire.

2. The composite wire of claim 1, wherein the radiopaque metal is selected from the group consisting of platinum, tantalum, gold, and combinations thereof.

3. The composite wire of claim 1, wherein the inner core is cylindrical.

4. The composite wire of claim 1, wherein the inner core is disposed centrally along a longitudinal axis of the composite wire.

5. The composite wire of claim 1, wherein the outer metal layer is formed of a superelastic alloy.

6. The composite wire of claim 1, wherein the outer metal layer is formed of a nickel-titanium alloy.

7. The composite wire of claim 1, wherein the composite wire is formed as a cylindrical wire.

8. A composite wire, comprising:
   a single wire having a first free end, a second free end, and a main body length therebetween for forming a vascular interventional device, said single wire including:

an elongated inner core having a selected length and formed from a first metal, said elongated inner core disposed centrally along a longitudinal axis of said single wire, and said first metal being radiopaque;

an outer metal layer coaxially disposed around said elongated inner core along the length of said elongated inner core, said outer metal layer being formed of a second metal different from said first metal; and a continuous intermediate polymer layer coaxially disposed between said outer metal layer and inner core, said continuous intermediate polymer layer being operative to insulate said elongated inner core and said outer metal layer from galvanic corrosion between said elongated inner core and said outer metal layer, said continuous intermediate polymer layer being formed from a polymer selected from the group consisting of poly-para-xylylene, a fluorine substituted poly-para-xylylene, and combinations thereof; and a segment of heat shrink tubing capturing the first free end of said single wire and the second free end of said single wire within the segment of heat shrink tubing to join the first free end of said single wire and the second free end said single wire together, said first and second free ends of said single wire overlapping in close proximity to each other such that said segment of tubing joining the first free end of said single wire and the second free end of said single wire together is configured to prevent said first and second free ends of said single wire from extending away from the main body length of said single wire.

9. The composite wire of claim 8, wherein the first metal is selected from the group consisting of platinum, tantalum, gold, and combinations thereof.

10. The composite wire of claim 8, wherein the inner core is cylindrical.

11. The composite wire of claim 8, wherein said second metal is a superelastic alloy.

12. The composite wire of claim 1, wherein said second metal is a nickel-titanium alloy.

13. The composite wire of claim 1, wherein the composite wire is formed as a cylindrical wire.

14. A composite wire, comprising:
a single wire having a first free end, a second free end, and a main body length therebetween for forming a vascular interventional device, said single wire including:
an elongated inner core having a selected length and formed from a first metal selected from the group consisting of platinum, tantalum, gold, and combinations thereof, said elongated inner core disposed centrally along a longitudinal axis of said single wire, and said first metal being radiopaque;

an outer metal layer coaxially disposed around said elongated inner core along the length of said elongated inner core, said outer metal layer being formed of a superelastic second metal different from said first metal; and a continuous intermediate polymer layer selected from the group consisting of poly-para-xylylene, a fluorine substituted poly-para-xylylene, and combinations thereof, said continuous intermediate polymer layer coaxially disposed between said outer metal layer and said elongated inner core, said continuous intermediate polymer layer being operative to insulate said elongated inner core and said outer metal layer from galvanic corrosion between said elongated inner core and said outer metal layer; and a segment of heat shrink tubing capturing the first and second free ends of said single wire within the segment of heat shrink tubing to join the first and second free ends of said single wire together, the first and second free ends of said single wire being in close proximity to each other, and said first and second free ends of said single wire overlapping such that said segment of tubing joining the first free end of said single wire and the second free end of said single wire together is configured to prevent said first and second free ends of said single wire from extending away from the main body length of said single wire.

15. The composite wire of claim 14, wherein the inner core is cylindrical and said composite wire is cylindrical.

16. The composite wire of claim 14, wherein said superelastic second metal is a nickel-titanium alloy.

17. The composite wire of claim 14, wherein said superelastic second metal is nitinol.

* * * * *